United States Patent [19]

Pilley

[11] Patent Number: 4,464,608
[45] Date of Patent: Aug. 7, 1984

[54] CIRCUIT FOR CONTROLLING OPTICAL APPARATUS SUCH AS AN OPHTHALMOSCOPE

[75] Inventor: H. Robert Pilley, Deering, N.H.

[73] Assignee: Warner Lambert Technologies, Inc., Southbridge, Mass.

[21] Appl. No.: 417,757

[22] Filed: Sep. 13, 1982

[51] Int. Cl.³ .................... H05B 41/32; A61B 3/14
[52] U.S. Cl. ................ 315/241 P; 315/232; 315/322; 351/206; 354/62
[58] Field of Search ............. 315/241 P, 322, 232, 315/324; 351/206, 207, 208; 354/62, 132, 137, 145; 128/6

[56] References Cited

U.S. PATENT DOCUMENTS

| 4,238,142 | 12/1980 | Richards et al. | 351/206 |
| 4,291,961 | 9/1981 | Takayama | 354/62 |
| 4,354,749 | 10/1982 | Hosoda | 354/62 X |

Primary Examiner—Eugene R. LaRoche
Attorney, Agent, or Firm—Alan H. Spencer

[57] ABSTRACT

A circuit for operating and controlling optical apparatus for viewing an object and making a photographic record thereof and having an illuminating light source and a photoflash light source, the circuit including a pulse width modulator for operating the illuminating light source, a flyback converter circuit and capacitor charging and discharging circuit for operating the photoflash light source, a clock pulse source connected to the pulse width modulator and the flyback converter for operating the same, and a delay circuit for allowing the optics to settle before operation of the photoflash. An energy level control circuit monitors the capacitor voltage and stops application of clock pulses to the flyback converter when the capacitor voltage reaches a desired value. A first visual indicator signals when the desired capacitor voltage is reached, a second visual indicator signals a certain condition in the apparatus, and a circuit gives priority to operation of the second indicator. Another photoflash light source and associated capacitor charging and discharging circuit is included, along with a switch for selectively controlling the connection of the flyback converter to either of the capacitor circuits for allowing operation of the photoflash light sources only one at a time. A protective diode network prevents a current surge from a charged capacitor circuit when one of the photoflash light sources and associated circuits is connected to the apparatus. An additional discharge path is provided for the capacitor circuit of the light source already connected to the apparatus when the other light source and circuit is subsequently connected to the apparatus. Each photoflash light source and associated capacitor charging and discharging circuit is provided with a branch for discharging stored energy when that light source and associated circuit is disconnected from the apparatus.

27 Claims, 6 Drawing Figures 4,464,608

CIRCUIT FOR CONTROLLING OPTICAL APPARATUS SUCH AS AN OPHTHALMOSCOPE

BACKGROUND OF THE INVENTION

This invention relates to the art of optical apparatus for viewing an object and making a photographic record thereof utilizing a photoflash light source, and more particularly to a new and improved electrical circuit for operating and controlling such apparatus.

One area of use of the present invention is in an ophthalmic examining and photographic recording instrument otherwise known as an ophthalmoscope, although the principles of the invention can be variously applied. Optical apparatus of this type includes an illuminating light source and a photoflash light source, and the circuit for controlling the operation of the light sources should include sections which co-operate in an efficient and effective manner to provide an instrument which is versatile and easy to use. With respect to control of the photoflash light source, some important considerations are control of the voltage for operation of the photoflash and enabling the system optics to reach a steady state condition before the photoflash is operated. Also, since such photoflash light sources are operated by discharge of a capacitor in a charge storing and discharge circuit associated therewith, it is important that the circuits be designed to prevent electrical hazards associated with connection and disconnection of such light sources and associated circuits from the apparatus. In addition, it would be highly desirable to incorporate integrated circuit chip technology in such circuits.

SUMMARY OF THE INVENTION

It is, therefore, a primary object of this invention to provide a new and improved circuit for operating and controlling optical apparatus for viewing an object and making a photographic record thereof and utilizing a photoflash light source.

It is a more particular object of this invention to provide a new and improved circuit for operating and controlling an ophthalmoscope.

It is a further object of this invention to provide a circuit for such optical apparatus which enables accurate and effective control of voltage for operating the photoflash light source and which allows the optics to reach a steady condition before operation of the photoflash light source.

It is a further object of this invention to provide a circuit for such optical apparatus which prevents electrical hazards when photoflash light sources are connected to and disconnected from the apparatus.

It is a further object of this invention to provide a circuit for such optical apparatus which utilizes the advantages of integrated circuit chip technology.

It is a more particular object of this invention to provide such a circuit for an ophthalmoscope wherein sections of the circuit co-operate in an efficient and effective manner to provide an instrument which is versatile and easy to use.

The present invention provides, in optical apparatus for viewing an object and making a photographic record thereof and having an illuminating light source and a photoflash light source, pulse width modulator circuit means for operating the illuminating light source, circuit means including a converter and capacitor charging and discharging circuit for operating the photoflash light source, and means for providing clock pulses to the pulse width modulator and to the converter for operating the photoflash and illuminating light source. An energy level control means monitors the capacitor voltage and stops application of clock pulses to the converter when the capacitor voltage reaches a desired value. A first visual indicating means signals when the desired capacitor voltage is reached, a second visual indicating means signals a certain condition in the apparatus, and a circuit gives priority to operation of the second indicating means. A delay circuit means provides a predetermined time delay between the occurrence of a command and the actual operation of the photoflash light source. The pulse width modulator, means for providing clock pulses, energy level control means and delay circuit means each includes a comparator, and the comparator each can be implemented by a corresponding one of a plurality of comparator stages of a single chip integrated circuit. Another photoflash light source and associated capacitor charging and discharging circuit can be provided, along with means for selectively controlling the connection of the converter to either of the capacitor circuits for allowing operation of the photoflash light sources only one at a time. There is provided protection means for preventing a current surge from a charged capacitor circuit when one of the photoflash light sources and associated circuits is connected to the apparatus, and means for defining an additional discharge path for the light source and circuit already connected to the apparatus when the other light source and circuit is subsequently connected to the apparatus. Each photoflash light source and associated capacitor charging and discharging circuit is provided with means for discharging stored energy when that light source and associated circuit is disconnected from the apparatus.

The foregoing and additional advantages and characterizing features of the present invention will become clearly apparent upon a reading of the ensuing detailed description together with the included drawing wherein:

BRIEF DESCRIPTION OF THE DRAWING FIGURES

Figure 2:
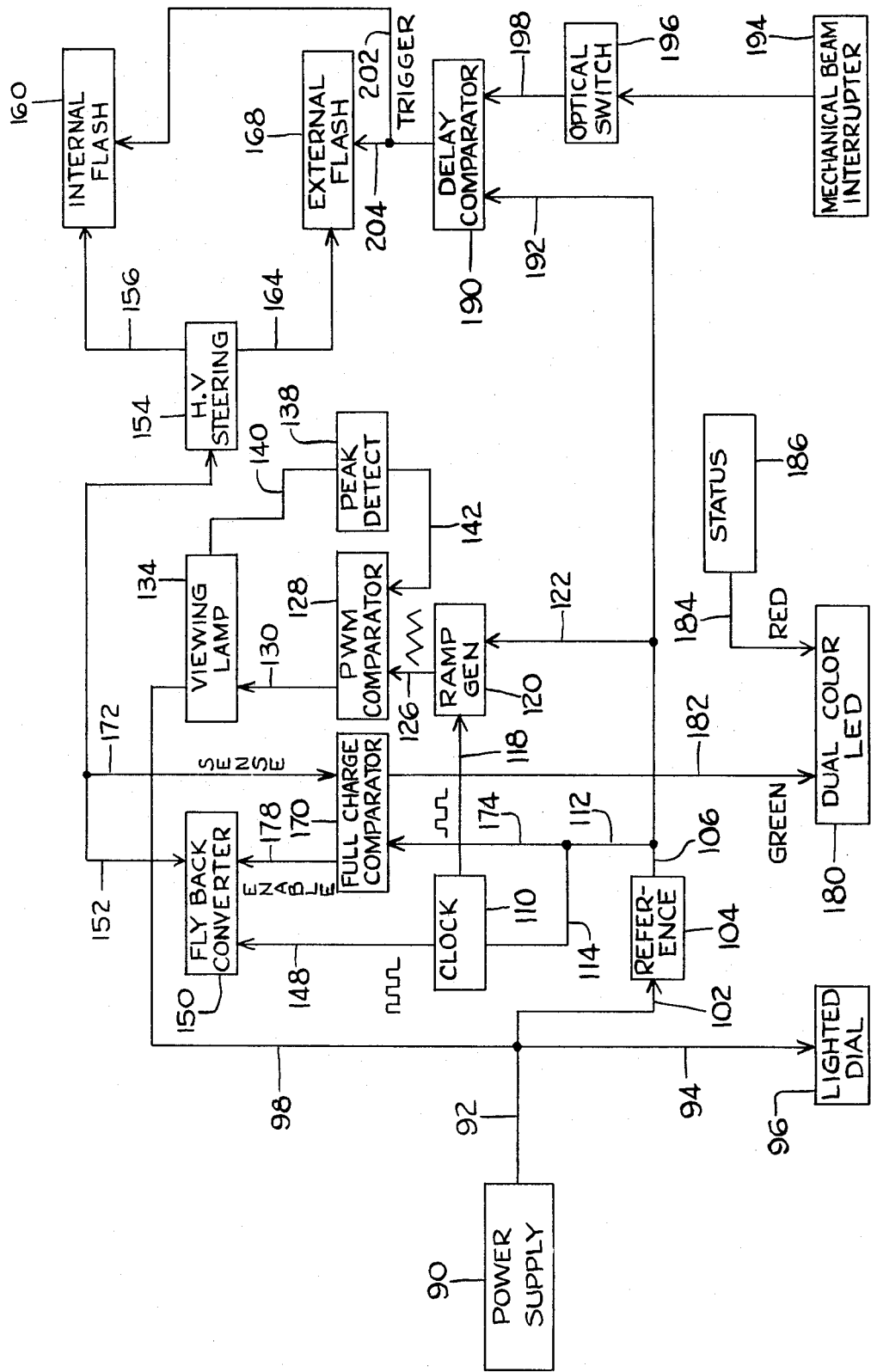
FIG. 2 is a block diagram of the circuit of the present invention for controlling optical apparatus.
Figure 5:
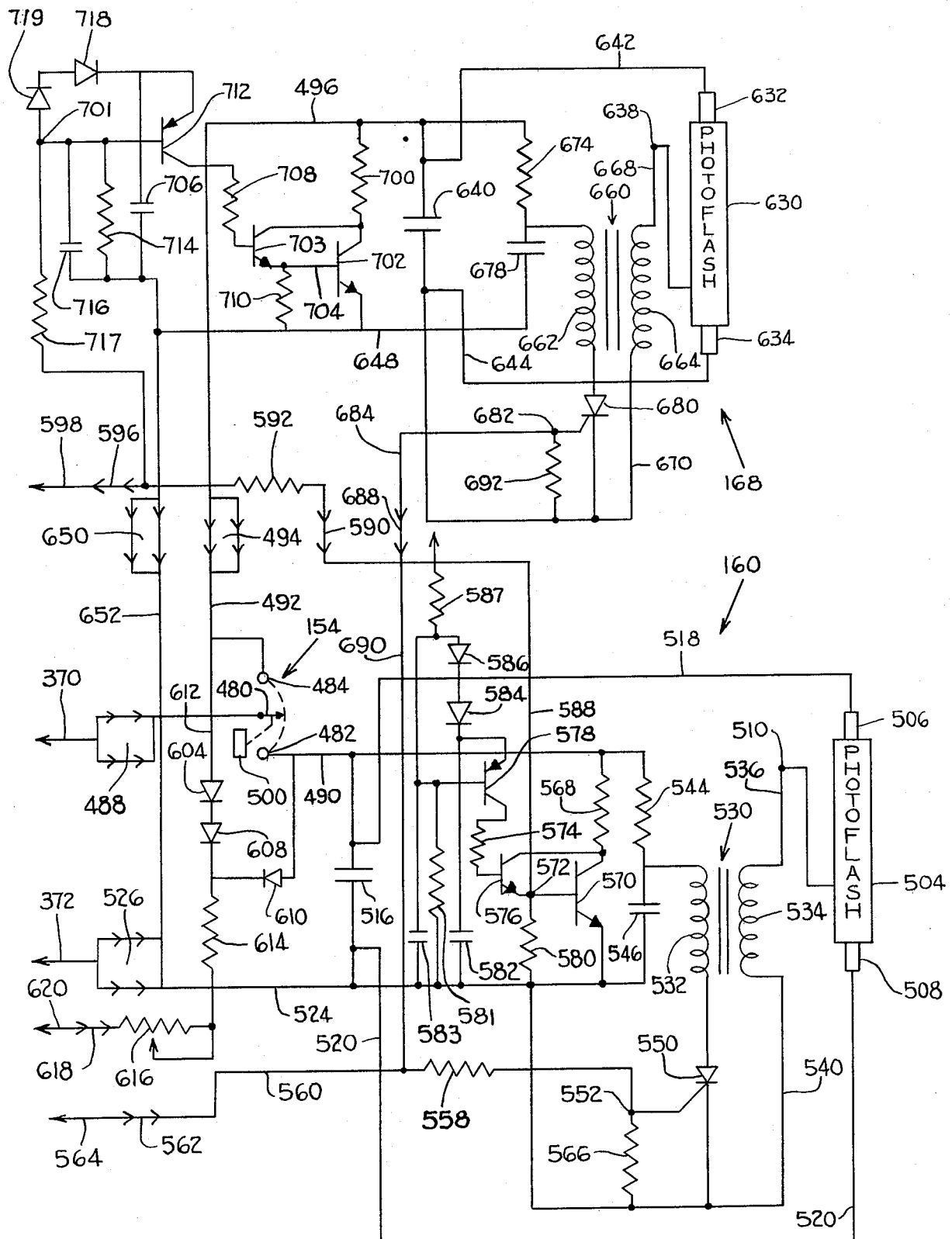
Figure 6:
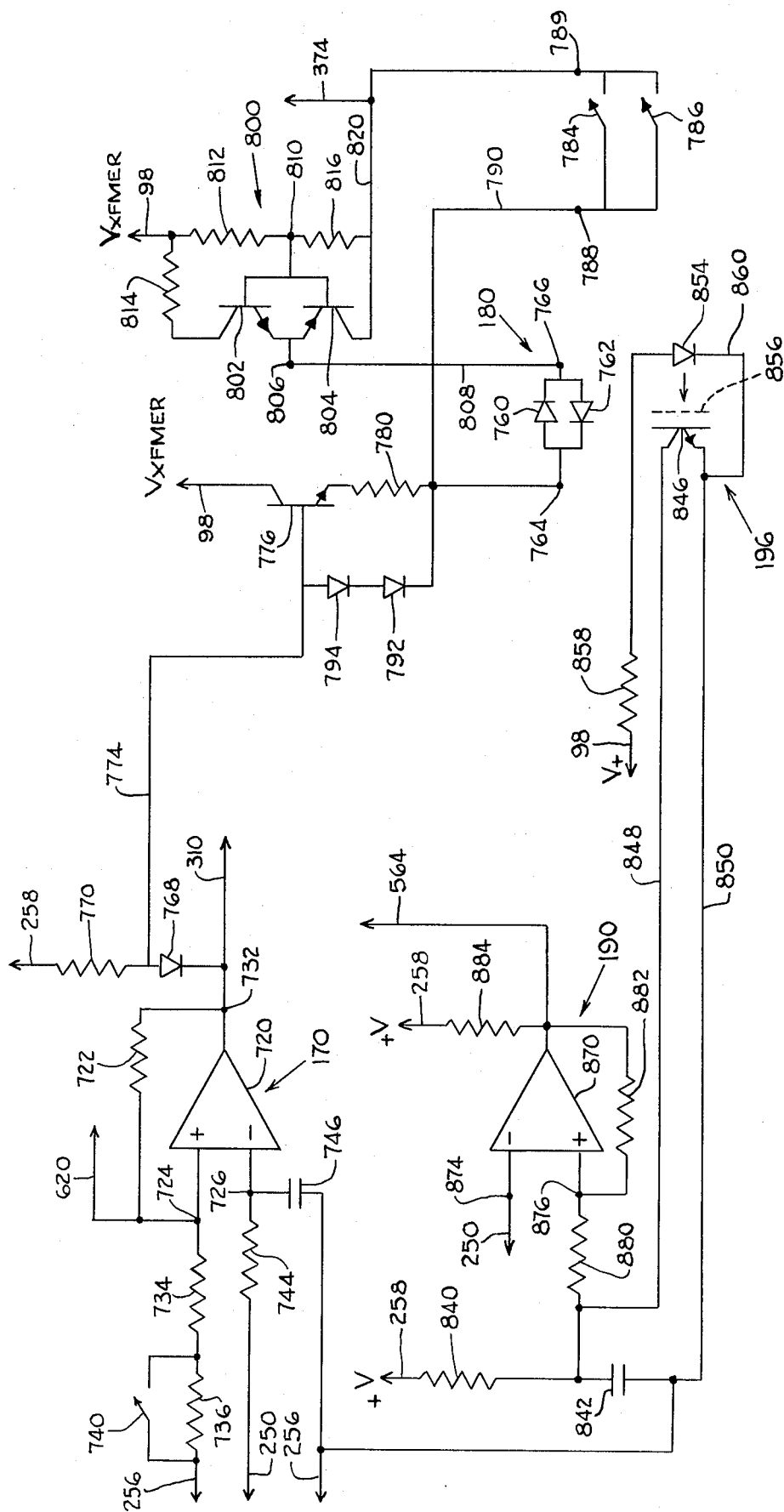

FIG. 5 is a schematic diagram of the portion of the circuit of FIG. 2 including the two photoflash light sources, associated capacitor charging and discharging circuits and high voltage steering means; and FIG. 6 is a schematic diagram of the portion of the circuit of FIG. 2 including the capacitor voltage monitor and control, visual indicating means and priority circuit therefor, and the optical delay circuit.

DETAILED DESCRIPTION OF THE ILLUSTRATED EMBODIMENT

Figure 1:
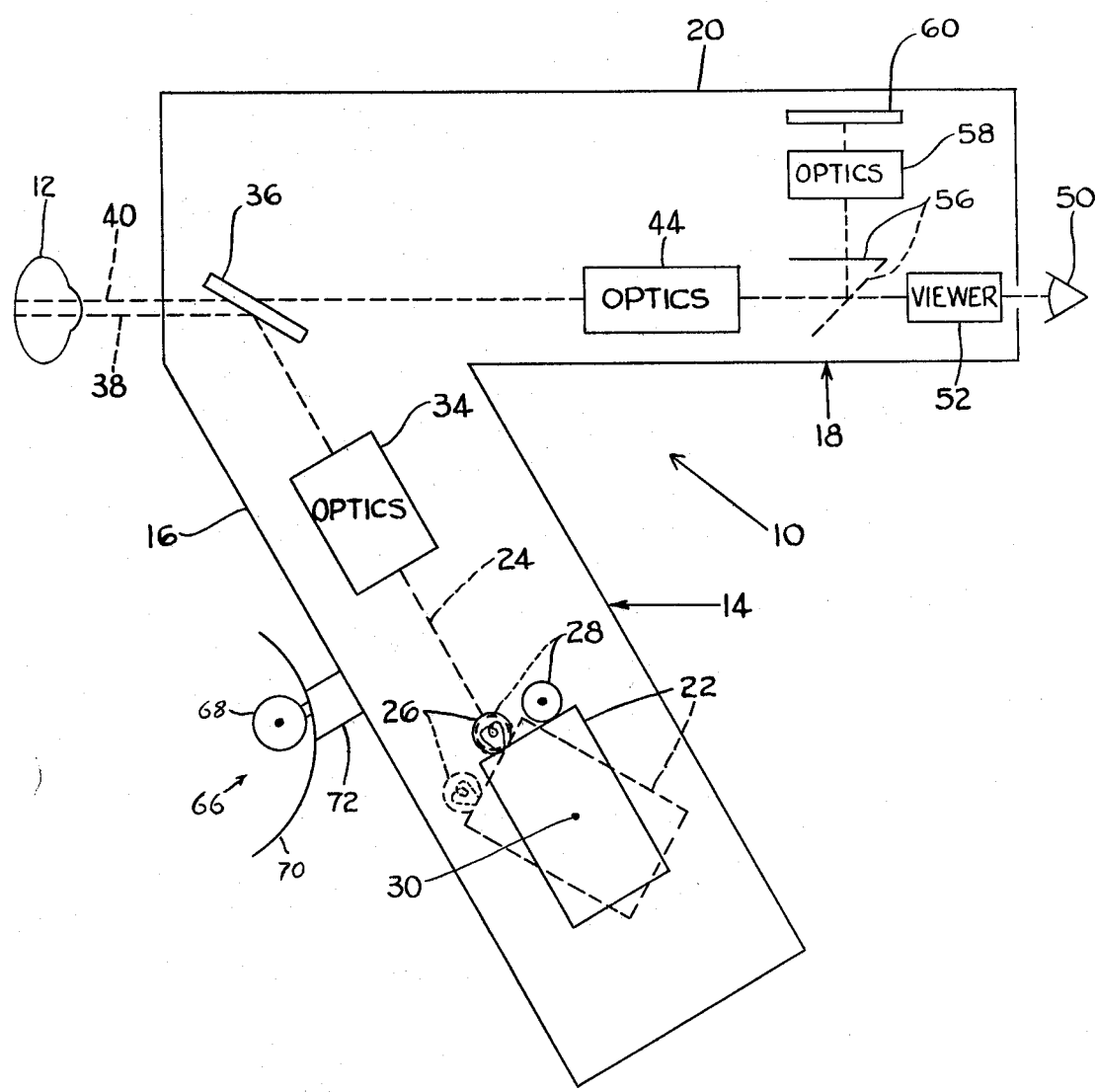
FIG. 1 is a diagrammatic illustration of a type of optical apparatus with which the circuit of the present invention is used.

Referring now to FIG. 1, there is shown a form of optical apparatus with which the circuit of the present invention is used in the form of an ophthalmoscope generally designated 10 for viewing and photographing the eye 12 of a patient. The instrument 10 includes a light input section 14 included generally within a housing portion 16 and a viewing and photographing portion 18 included generally within a housing portion 20. The light input portion of the apparatus includes a component shown schematically at 22 for providing input light along an axis or path 24. The light input portion includes an electrically-operated illuminating light source 26 which typically is an incandescent lamp, preferably of the gas-filled type, and a photoflash light source 28 typically in the form of a tubular photoflash lamp. In the illustrative arrangement shown, the apparatus portion 22 is pivotable about an axis 30 as indicated by the broken lines in FIG. 1 for selectively placing first one of the light sources 26,28 and then the other light source into alignment with the axis or path 24. Other arrangements can of course be employed. The light input section further includes optics generally designated 34 along path 24, and the optics 34 can include an arrangement of diaphragms or the like for controlling the size of an aperture in the light path and lenses for receiving and directing the light input. The light input travels further to a beam splitter 36 for reflecting a portion of the light, indicated by the path 38, to the eye 12 for illuminating the same. A portion of this light is reflected from within the eye 12, for example from the fundus of the eye, as indicated by the path 40 and travels along the viewing and photographing portion 18 through optics generally designated 44 for imaging and for erecting the reflected image of the eye 12. This image is viewed by the eye 50 of the practitioner examining the patient through an eyepiece 52 of the apparatus. The photographing and recording portion of the apparatus includes a movable mirror 56, appropriate optics 58 and a film plane designated 60. The mirror 56 is shown in solid line position during the viewing mode, and it is movable to the broken line position during photographing whereby it focuses the image received from the eye through the optics 58 to the film plane 60 for photographic recording thereon. During the viewing mode, light source 26 is in alignment with path 24 while the practitioner examines the eye and makes adjustments in the apparatus for photographic purposes. During the photographing mode, the photoflash light source 28 is moved into alignment with path 24 as light source 26 is moved away, and when source 28 is in position it is operated to produce a photoflash after mirror 56 reaches the broken line position shown in FIG. 1.

The foregoing description has been by way of illustration to show a form of optical apparatus with which the circuit of the present invention is utilized. For a more detailed description of such illustrative apparatus, reference may be made to U.S. Pat. No. 4,238,142 issued Dec. 9, 1980, entitled "Method and Apparatus For Examining and Photographing the Ocular Fundus" and assigned to the assignee of the present invention.

In accordance with the present invention, the optical apparatus can be provided with an additional photoflash light source generally designated 66 in FIG. 1. In the particular use with an ophthalmoscope, the additional photoflash light source can be employed in photographing portions of the patient's face as will be described further on in the specification. Briefly, light source 66 includes a lamp 68 which typically is a tubular photoflash lamp, a reflector 70, and energy storing and releasing circuit means (not shown in FIG. 1) for the lamp and means generally designated 72 for connecting the light source to the instrument housing and completing an electrical circuit to lamp 68 which connection preferably is removable or releasable.

FIG. 2 is a block diagram of the circuit according to the present invention. A power supply generally designated 90 provides output voltage on line 92 which is regulated d.c., preferably having a magnitude of 13 volts positive. Typically, the input to power supply 90 is line a.c. voltage, and power supply 90 would include a power transformer having the primary thereof connected to the line, a bridge rectifier connected to the transformer secondary winding, a filter connected to the output of the rectifier and a voltage regulator connected to the filter. The regulated output voltage on line 92 can be connected by a line 94 to a dial 96 on the instrument for illumination thereof. Line 92 also is connected by a line 98 to the relatively higher power loads in the circuit including the illumination light source or viewing lamp and to the photoflash capacitor charging circuit in a manner which will be described. In addition, the regulated voltage output on line 92 is connected by a line 102 to a component generally designated 104 which provides reference and bias voltage for various elements in the circuit. Component 104 includes a regulator and associated circuit elements which will be described in detail presently, and an output of component 104 is designated 106.

The circuit of the present invention includes a single chip integrated circuit having a plurality of comparator stages which, in turn, are used to provide various circuit functions for controlling the illuminating and photoflash light sources of the optical apparatus. The comparator stages of the integrated circuit will be described in detail presently. As shown in FIG. 2, one comparator stage generally designated 110 is employed to provide a source of system clock pulses. Voltage for operating the clock pulse source 110 is obtained from reference component 104 through lines 112,114 connected to output 106 of component 104. The clock pulses, in turn, are utilized for operation of the viewing lamp and for charging of the capacitor for each photoflash light source. In particular, for operating the viewing lamp clock pulses are applied by line 118 to an input of a ramp waveform generating circuit 120. Reference voltage for generator 120 is obtained from reference component 104 through line 122 connected to output 106. The waveform output of generator 120 is applied by a line 126 to one input of a pulse width modulator circuit 128 which is another stage of the integrated circuit comparator previously described. Pulses of adjustable width from modulator 128 are applied by a line 130 to the illumination light source or viewing lamp generally designated 134 in FIG. 2. The viewing lamp designated 134 in FIG. 2 represents the illuminating light source 26 shown in the illustrative instrument of FIG. 1, and lamp preferably is of the type wherein the intensity of the light output is proportional to the width of electrical pulses applied thereto, for example a gas-filled lamp. The light intensity of lamp 134 is adjusted by means of a feedback circuit including a peak detector component 138 having an input connected by line 140 to lamp 134 and having an output connected by line 142 to another input of comparator 128 in a manner which will be described.

Clock pulses from comparator stage 110 also are used to operate the photoflash light source, and for this purpose are applied by a line 148 to the input of a flyback converter circuit generally designated 150 which includes a flyback transformer and which will be described in further detail presently. The output voltage from circuit 150 is applied by line 152 to a high voltage steering component designated 154 which, in turn, controls the application of the high voltage to either of the photoflash light sources. In particular, component 154 selectively connects the high voltage to either line 156 leading to a first photoflash light source and associated circuitry generally designated the internal flash 160 in FIG. 2, or to a line 164 leading to a second photoflash light source and associated circuitry generally designated the external flash 168 in FIG. 2. The output voltage from converter 150 on line 152 is monitored by a comparator designated 170, which is another stage of the aforementioned integrated circuit, having an input connected by line 172 to line 152. Reference voltage for comparator 170 is obtained from component 104 through lines 174 and 112. When a predetermined condition exists between the sensed voltage on line 172 and a reference voltage, the comparator stage 170 allows continued operation of the flyback converter 150 by means of an enable signal on line 178 from comparator 170 to converter 150. One method for accomplishing this, as will be described, is control of the application of clock pulses on line 148 to the converter circuit 150.

The circuit of FIG. 2 further includes first and second visual indicating means which are designated collectively 180. The visual indicating means can comprise, for example, a pair of light emitting diodes of different colors and energized in response to certain conditions in the circuit. One condition is when the voltage on line 152 reaches a predetermined level as signalled by comparator 170, and to this end a line 182 is connected from comparator 170 to one visual component of the indicating means 180. The other visual component of indicating means 180 is connected by a line 184 to a component or mechanism designated 186 in the apparatus for signalling a predetermined condition or status thereof as will as described. This, for example, can be a certain mechanical condition of the camera in the optical instrument.

The circuit of FIG. 2 further includes delay circuit means generally designated 190 operatively connected to each photoflash light source and to means for commanding operation of the photoflash light source for providing a predetermined time delay between the occurrence of a command and the actual operation of the photoflash light source. The delay circuit means 190 is another comparator stage of the previously described integrated circuit, and reference voltage is obtained from reference component 104 through line 192. A signal indication of the command is provided by an electro-optical arrangement including a mechanical beam interrupter generally designated 194 which interrupts an optical beam to influence operation of an optical switch generally designated 196 which, in turn, is connected by line 198 to an input of the comparator 190. Briefly, the light beam from a light emitting diode to a phototransistor is interrupted initiating charging of a capacitor wherein the delay is determined by the time constant of the capacitor and a resistor associated therewith, whereupon after the predetermined time delay the comparator 190 produces a signal on lines 202,204 leading to the internal and external flashes 160 and 168, respectively for triggering whichever has been charged under control of the high voltage steering means 154.

Figure 3:
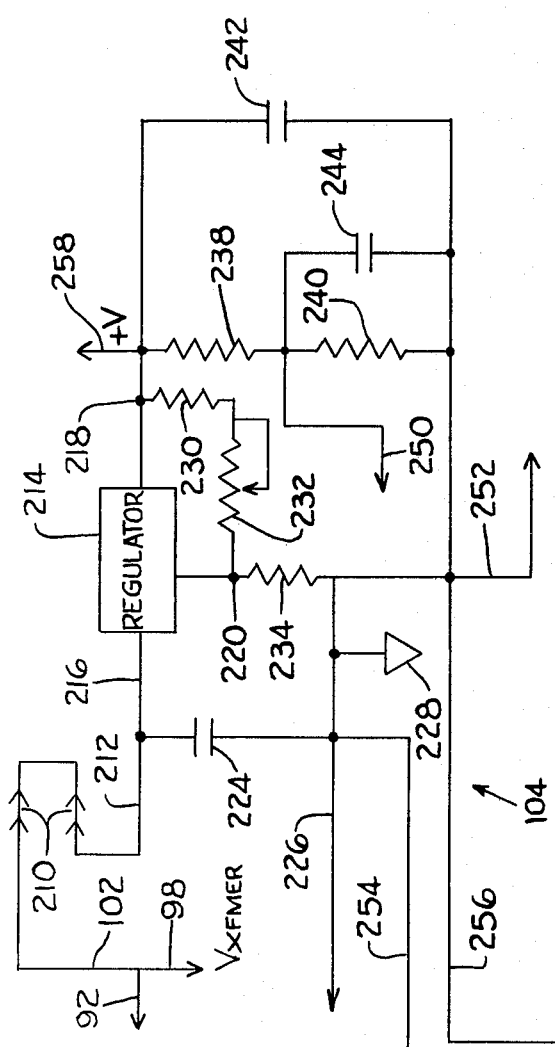
FIG. 3 is a schematic diagram of the portion of the circuit of FIG. 2 including the regulation circuit, clock pulse generator and flyback converter.
Figure 3:
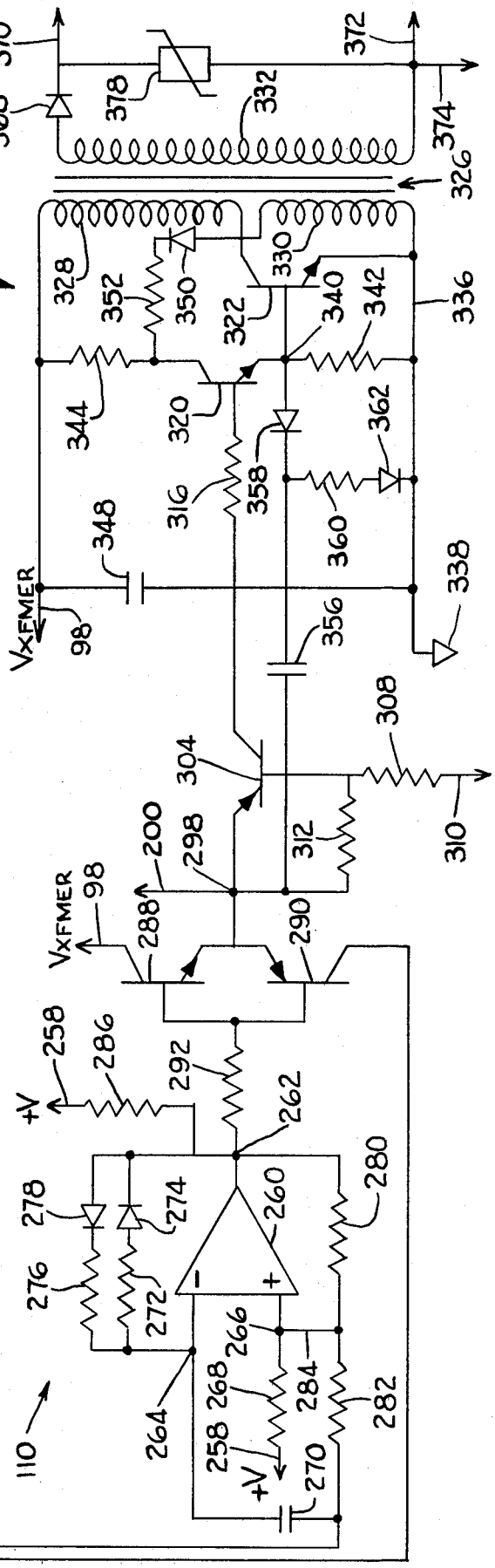

FIG. 3 shows in further detail the circuits for the reference component 104, the clock pulse generator 110 and the flyback converter 150. Power input from power supply 90 on line 92 is divided into a first path corresponding to line 98 for connection to the high power loads such as the viewing lamp designated 134 in FIG. 2 and the flyback converter 150. For convenience, this voltage is designated $V_{XFMER}$ in FIG. 3. The other path includes a safety interlock between the circuitry and the flash units. This is shown in FIG. 3 wherein an interlock designated 210 is connected between line 102 and a line 212 leading to the input of the reference circuit 104. Thus, when a flash circuit is removed while the power is on, high voltage portions of the circuit such as flyback converter 150 are turned off before the flash unit is completely disconnected and removed for purposes of safety. Circuit 104 includes a voltage regulator 214 having an input terminal 216, an output terminal 218, and a voltage adjusting terminal 220. An input capacitor 224 is connected between terminal 216 and a line 226 connected to power supply 90 and to an internal ground or reference 228. The series combination of a fixed resistor 230 and a variable resistor 232 is connected between regulator terminals 218 and 220, and another resistor 235 is connected between terminal 220 and the reference 228. A voltage divider comprising the series combination of resistors 238 and 240 is connected from regulator output terminal 218 to reference 228. A capacitor 242 is connected across the voltage divider, and another capacitor 244 is connected across resistor 240. The junction of resistors 238,240 is connected by line 250 to various points in other portions of the circuit as will be described. Circuit 104 is connected by line 252 to the viewing lamp circuit, and is connected by lines 254,256 to the clock pulse source 110. The output terminal 218 of regulator 214 is connected by line 258 to other portions of the circuit as will be described, and the voltage on line 258 is designated $+V$.

By way of example, in an illustrative circuit, regulator 214 is commercially available under the designation LM 317 and provides a 9.5 volt reference which is set by resistor 232 to 9.5 volts plus or minus 0.05 volts. Resistors 238 and 240 are each of a magnitude of one kilohm and divide the reference down to five volts. Each of the capacitors 224 and 242 has a magnitude of 22 microfarads and capacitor 244 has a magnitude of 0.1 microfarad. Resistor 230 has a magnitude of 1.2 kilohm, resistor 232 a maximum magnitude of 0.5 kilohm and resistor 234 a magnitude of 10 kilohms.

The clock pulse source 110 includes a comparator 260 having an output terminal 262, an inverting input terminal 264 and a non-inverting input terminal 266. Input terminal 266 is connected through an input resistor 268 to the positive reference voltage $+V$ provided by circuit 104 on line 258. Input terminal 264 is connected through an input capacitor 270 to line 256 from circuit 104. The comparator output terminal 262 is connected through a resistor-diode network to input terminal 264, the network comprising a first series combination of a resistor 272 and diode 274 and a second series combination of a resistor 276 and reverse-poled diode 278, the two series combination being connected in parallel. Output terminal 262 is connected through the series combination of resistors 280 and 282 to line 256 from reference circuit 104, and the junction of resistors 280,282 is connected by a line 284 to input terminal 266. Output terminal 262 also is connected through a resistor 286 to the reference voltage +V provided by circuit 104 on line 258.

The pulse waveform output provided by the comparator 260 and associated circuit is present on output terminal 262, and this is buffered by a complementary pair of transistors including an NPN transistor 288 and a PNP transistor 290. Output terminal 262 is connected through a resistor 292 to the common base terminals of transistors 288,290, the collector terminal of transistor 290 is connected to line 254 from circuit 104, and the collector terminal of transistor 288 is connected to line 98 on which the power supply voltage $V_{XFMER}$ is available. A buffered square wave output is provided on terminal 298 connected to the common emitters of transistors 288,290. This buffered square wave output is used for various functions in the circuit, and to this end terminal 298 is connected by line 200 to the pulse width modulator circuit for operating the illuminating light source, and terminal 298 also is connected in a controlled manner to the flyback converter circuit for providing voltage to charge the capacitors of the photoflash light sources, both of which will be described in detail presently.

By way of example, in an illustrative circuit, comparator 260 is one-quarter of a single chip integrated circuit comparator commercially available under the designation LM 339. thus the comparator stage 260 is dedicated to the system clock function. Capacitor 270 has a magnitude of 0.001 microfarads, each of the resistors 268,280 and 282 has a magnitude of 100 kilohms, and each of the resistors 286 and 292 has a magnitude of 1 kilohm. Resistor 272 has a magnitude of 143 kilohms and resistor 276 has a magnitude of 16.2 kilohms. The output on terminal 262 of comparator 260 is high for about 12 microseconds and low for about 100 microseconds during each period, and the buffered square wave output on terminal 298 has a frequency of about 9 kilohertz.

The output of clock pulse source 110 is connected in a controlled manner to the flyback converter 150 which, briefly, converts electrical pulses applied thereto into energy to be stored for use in operating the photoflash light sources. The output signal on terminal 298 is connected to the flyback converter 150 through normally closed controlled switching means in the form of PNP transistor 304 to the flyback converter 150. In particular, the emitter terminal of transistor 304 is connected to terminal 298 and the base terminal thereof is connected through a resistor 308 to the comparator circuit 170. Thus, when the voltage on the capacitor associated with either photoflash light source is below the desired value, the comparator output is low and is applied through resistor 308 to the base terminal of transistor 304 maintaining it conducting to allow transmission therethrough of the pulses from clock source 110. On the other hand, when the capacitor voltage reaches the desired value, the comparator output becomes high thereby turning off transistor 304 to stop application of clock pulses. A resistor 312 is connected in the base-emitter circuit of transistor 304.

The collector terminal of transistor 304 is coupled through a resistor 316 to the base of a Darlington pair of NPN transistors 320 and 322. The conversion circuit 150 includes a flyback transformer 326 having a pair of primary windings 328,330 and a secondary winding 332. One terminal of primary winding 328 is connected to line 98 from the power supply. The other terminal of primary winding 328 is connected to the collector of transistor 322. The emitter terminal of transistor 322 is connected to a line 336 which, in turn, is connected to an internal ground or reference 338. The emitter-base connection 340 of the Darlington pair is connected through a resistor 342 to line 336. The collector of transistor 320 is connected through a resistor 344 to line 98. An input capacitor 348 is connected between lines 98 and 336.

The additional primary winding 330 is used to provide regenerative base drive to the Darlington transistors 320,322. One terminal of winding 330 is connected to the anode of a diode 350, the cathode of which is connected through a limiting resistor 352 to the collector of transistor 320. The other terminal of winding 330 is connected to reference line 336. Resistor 352 limits the base drive to the transistors 320,322. When transistor 304 turns off to stop application of the clock pulses to converter 150, the transistor 322 is turned off very quickly and a capacitor 356 is employed to pull the base of transistor 322 negatively through a diode 358 to turn it off very quickly. In particular, one terminal of capacitor 356 is connected to the output terminal 298 of the clock pulse source, and the other capacitor terminal is connected to the cathode of the diode 358, the anode of which is connected to the emitter-base connection 340 of the transistor pair. The cathode of diode 358 also is connected through a resistor 360 and a diode 362 to the reference line 336.

One terminal of secondary winding 332 is connected to the anode of a diode 368, the cathode of which is connected to a first output line 370, the other terminal of winding 332 being connected to a second output line 372. The output of circuit 150, in turn, is connected under control of the high voltage steering component 154 to the charging circuits for the photoflash light sources in a manner which will be described. Line 374 also connects the one winding terminal to another portion of the circuit in a manner which will be described. A metal oxide varistor 378 is connected across output lines 370,372 to clamp the voltage to a safe level and to protect transistor 322 during internal flash removal, when power is on.

During the time that transistor 304 is on, the buffered positive clock pulses at terminal 298 are applied to the base of the complementary Darlington pair of transistors 320,322. The positive pulse turns on the transistor pair, and while transistor 322 is on, the voltage at the end of transformer winding 328, connected to the collector of transistor 322, is about 0.4 volts. This causes current to flow in the primary of transformer 326. Winding 330 provides regenerative base drive to transistors 320 and 322, and the limiting resistor 352 limits the base drive to the transistors. The transformer primary circuit continues to rise to about 3 amperes until the clock pulse goes low. When that happens, transistor 322 is turned off very quickly. Capacitor 356 pulls the base of transistor 322 negative through diode 358 turning transistor 322 off very quickly. The transformer secondary winding 322 flies back and charges the capacitor of the photoflash light source in a manner which will be described. This capacitor charges at a three watt rate giving a full charge time to 30 joules of about 10 seconds. The operation of transformer 326 is governed by the relationship $\frac{1}{2}LI^2 = \frac{1}{2}CV^2$ where L is the primary inductance, I is the primary current, C is the capacitance of the flash capacitor, and V is the voltage on that capacitor. The capacitor will continue to charge at the 3 watt rate until a predetermined reference voltage is reached with the result that transistor 304 is turned off in a manner which will be described in detail presently.

The metal oxide varistor 378 clamps the positive secondary voltage to under 400 volts, if the photoflash light source should happen to be removed while electrical power is being supplied to the apparatus. Normally, the apparatus is constructed so that the transformer voltage is disconnected at the same time as the flash capacitor, but the possibility does exist for the capacitor to be removed before the transformer primary voltage is disconnected. Under such conditions the flyback voltage could go to an extremely high value and damage the transistors 320,322. Accordingly, the metal oxide varistor 378 is employed to clamp the voltage to a safe level.

By way of example, in an illustrative circuit, each of the resistors 308,312 and 316 has a magnitude of 1 kilohm, each capacitor 348 and 356 has a magnitude of 0.1 microfarad, resistor 342 has a magnitude of 220 ohms, resistor 344 has a magnitude of 270 ohms, resistor 352 has a magnitude of 5.6 ohms and resistor 360 a magnitude of 56 ohms. The varistor 378 is of the type commercially designated V275LA2.

Figure 4:
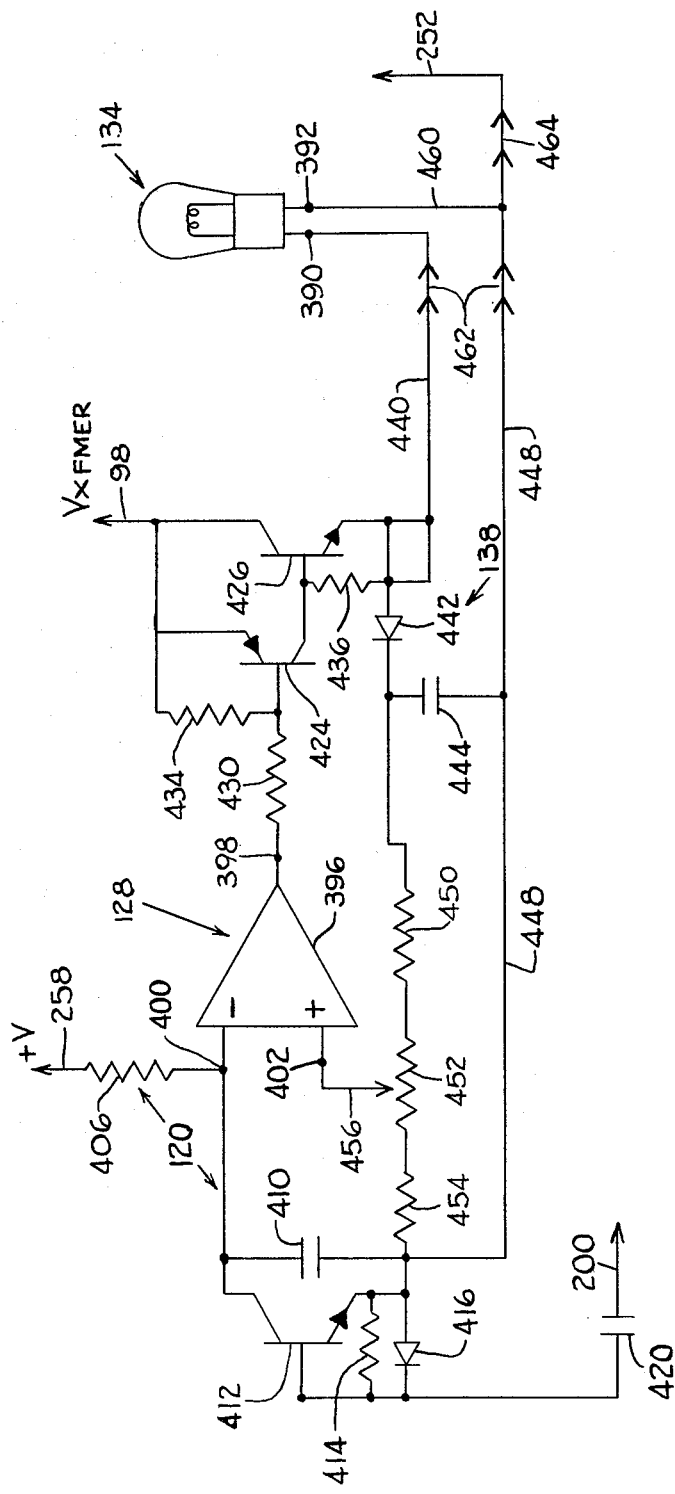
FIG. 4 is a schematic diagram of the portion of the circuit of FIG. 2 including the illuminating light source and pulse width modulator circuit for operating the light source.

FIG. 4 shows in further detail the circuits for ramp generator 120, pulse width modulating comparator 128, and peak detector 138 associated with viewing lamp 134. Lamp 134 is of the type wherein the light intensity is proportional to the width of the electrical pulses applied thereto, and typically is a gas-filled lamp of the incandescent type. As shown in FIG. 4, lamp 134 has a pair of terminals 390,392 extending from the base thereof. Comparator 128 comprises another comparator stage 396 of the single chip integrated circuit and has an output terminal 398, an inverting input 400 and a non-inverting input 402. Input terminal 400 is connected through a resistor 406 to line 258 leading to the positive voltage supply +V of FIG. 3. The inverting input terminal 400 also is connected to one terminal of a capacitor 410. Resistor 406 and capacitor 410 comprises a ramp waveform generator as will be described presently. A transistor 412 is connected across capacitor 410. In particular, the collector terminal of transistor 412 is connected to the terminal of capacitor 410 connected to comparator input terminal 400, and the emitter of transistor 412 is connected to the other terminal of capacitor 410. The combination of a resistor 414 and diode 416 is connected in the base-emitter circuit of transistor 412 with the anode of the diode connected to the emitter and the cathode thereof to the base. The base terminal of transistor 412 also is connected through a differentiating capacitor 420 to line 200 from the output of clock pulse generator 110 of FIG. 3.

The output of comparator 396 on terminal 398 is applied to a complementary Darlington pair comprising transistors 424 and 426. In particular, comparator output terminal 398 is connected through a resistor 430 to the base terminal of transistor 424. A resistor 434 is connected in the base-emitter circuit of transistor 424. The collector terminal of transistor 426 is connected to line 98 from the power supply providing the voltage $V_{XFMER}$, and a resistor 436 is connected in the base-emitter circuit of transistor 426. The emitter terminal of transistor 426 is connected by line 440 to lamp terminal 390 whereby the output of the complementary Darlington pair is applied to lamp 134.

The combination of a diode 442 and capacitor 444 comprises the peak detector 138. In particular, the anode of diode 442 is connected to the emitter terminal of transistor 426, and the cathode of diode 442 is connected to one terminal of capacitor 444. The other terminal of capacitor 444 is connected to a circuit reference line 448. The junction of diode 442 and capacitor 444 is connected through the series combination of a fixed resistor 450, a variable resistor 452 and another fixed resistor 454 to the junction of the terminal of capacitor 410 and the emitter terminal of transistor 412. This junction also is connected to reference line 448. The wiper arm of variable resistor 452 is connected by line 456 to the non-inverting input terminal 402 of comparator stage 396. Reference line 448 is connected through a line 460 to the other lamp terminal 392, and it also is connected to line 252 from the regulator 104 in the circuit of FIG. 3. An interlock 462 can be included in lines 440 and 448 as shown in FIG. 4, and another interlock 464 can be included in the connection of line 448 to line 252.

The low impedance output signal from transistors 288,290 at terminal 298 in the circuit of FIG. 3 is differentiated by capacitor 420 in the circuit of FIG. 4 and applied to the base terminal of transistor 412. Transistor 412 operates to reset the ramp waveform generated by the combination of resistor 406 and capacitor 410 on each positive-going edge of the buffered clock pulse square wave output signal. The ramp waveform generated on capacitor 410 is applied to the inverting input terminal 400 of comparator 396. In the illustrative circuit shown, normally this ramp waveform has an amplitude of 4.5 volts and a frequency equal to that of the system clock pulses. The output of comparator 396 is fed to the complementary Darlington pair of transistors 424,426, and the output of transistor 426 is fed to the gas-filled viewing lamp 134 to operate the same. The peak voltage detector comprising diode 442 and capacitor 444 stores the peak voltage across lamp 134 on the capacitor 444. This voltage then is fed through the resistive divider network comprising resistors 450,452 and 454, and the voltage on line 456 from the wiper arm of resistor 452 is applied to the non-inverting terminal 402 of comparator 396 to provide negative feedback. This negative feedback provides lamp intensity regulation for changes in the voltage $V_{XFMER}$. The intensity of the viewing lamp 134 is controlled by the variable resistor 452. The duty cycle for the lamp 134 in the circuit shown varies from about 55% for full light intensity to about 20% for low intensity.

By way of example, in an illustrative circuit, capacitor 420 has a magnitude of 0.002 microfarads, resistor 414 has a magnitude of 2 kilohms, capacitor 410 has a magnitude of 0.001 microfarads and resistor 406 has a magnitude of 182 kilohms. Resistors 450,452 and 454 have magnitudes of 102 kilohms, 100 kilohms and 80.6 kilohms, respectively. Resistors 430 and 434 both have magnitudes of 1 kilohm, resistor 436 has a magnitude of 220 ohms and capacitor 444 has a magnitude of 0.1 microfarads.

FIG. 5 illustrates in further detail the first and second photoflash light sources and associated energy storing and releasing means together with the high voltage steering means according to the present invention as shown in FIG. 2. In particular, there is the first photoflash light source and associated energy storing and releasing means which is designated the internal flash 160 in the system of FIG. 2. There is also provided a second photoflash light source and associated energy storing and releasing means which is designated the external flash in 168 in FIG. 2. The internal and external photoflash units 160 and 168, respectively, are connected to each other and to other portions of the circuit through safety interlocks which will be identified during the detailed description of FIG. 5. There is also provided switching means also called the high voltage steering means 154 in FIG. 2, for connecting the output of the conversion circuit 150 to either of the energy storing and releasing means for causing energy to be stored in only one of the energy storing and releasing means at a time.

As shown in FIG. 4, the switching means 154 has a switch arm 480 movable between a pair of switch contacts 482,484. Switch arm 480 is connected by a line 486 and a safety interlock 488 to line 370 from the output of the flyback converter circuit 150. Switch contact 482 is connected by line 490 to the energy storing and releasing circuit associated with the internal photoflash light source of unit 160. Switch contact 484 is connected by a line 492 through a safety interlock 494 and a line 496 to the energy storing and releasing circuit for the external photoflash light source 168. According to a preferred mode of the present invention, the switching means 154 normally is in a first state with switch arm 480 engaging contact 482 to apply voltage to the circuit associated with the internal photoflash light source of unit 160. There is provided operator means designated 500 which can be mechanically associated with the second photoflash light source and associated circuit of unit 168 for changing the switching means 154 to the second state where arm 480 engages contact 484 when the second or external photoflash unit 168 is connected to the apparatus.

Referring now to the first or internal flash unit 160, there is a photoflash lamp 504 of the tubular type having a pair of terminals 506,508 at opposite ends thereof for applying a relatively high direct voltage thereto. Lamp 504 corresponds to lamp 26 in the illustrative arrangement of FIG. 1 and is mounted in the apparatus by suitable means. Lamp 504 also is provided with a third terminal 510 intermediate the terminals 506,508 for applying a relatively high trigger voltage for operating the same in a manner which will be described. Voltage for application to the lamp terminals 506, 508 is obtained from a capacitor 516. One terminal of capacitor 516 is connected by a line 518 to lamp terminal 506, and the opposite terminal of capacitor 516 is connected by a line 520 to lamp terminal 508. The one capacitor terminal also is connected to line 490 whereby voltage from the flyback converter 150 can be applied to capacitor 516 for charging the same, and a return path to the circuit 150 from the opposite terminal of capacitor 516 is provided by a line 524 through an interlock 526 to line 372 from circuit 150.

Trigger voltage for operating lamp 504 is provided by a trigger transformer 530 having a primary winding 532 and a secondary winding 534. One terminal of the transformer secondary winding is connected by line 536 to the lamp trigger terminal 510. The other terminal of winding 534 is connected by a line 540 to line 524. One terminal of the transformer primary winding 532 is connected through a current limiting resistor 544 to line 490, and the same terminal is connected through a capacitor 536 to line 524, the capacitor 536 providing a low impedance source for the primary winding. The other terminal of winding 532 is connected to the anode of a silicon controlled rectifier 550, the cathode of which is connected to line 540. The control or gate terminal 552 of rectifier 550 is connected through a resistor 558, a line 560, an intelock 562 and a line 564 to the delay comparator 190 and associated circuit for providing a trigger signal to operate the photoflash lamp in a manner which will be described.

Normally, the discharge path for capacitor 516 is through lamp 504 when a trigger voltage is applied to terminal 510. For reasons of safety, the circuit of the present invention includes an additional or secondary discharge path for capacitor 516 as follows. The additional discharge path includes the series combination of a resistor 568 and a semiconductor switching means in the form of a transistor 570 connected across capacitor 516. In particular, one terminal of resistor 568 is connected to line 490, the other terminal of resistor 568 is connected to the collector of transistor 570, and the emitter terminal thereof is connected to line 524.

Transistor 570 normally is turned off so that the additional discharge path normally is opened. Transistor 570 is turned on thereby closing the switch to complete the secondary discharge path through resistor 568 and transistor 570 in the following manner. There is provided a circuit which supplies drive for transistor 570, which circuit means is activated in response to disconnection of the internal flash unit 160 from the apparatus or by the removal of the apparatus power. The circuit means includes an energy storage capacitor 582 which is charged through resistor 587 and series diodes 584 and 586. Resistor 587 is connected to circuit 104, such as through interlock 210. Transistor switch 578 is off when power is applied. The instant that power is removed either by the disconnection of the internal flash 160 or by shutting off the apparatus, transistor 578 is forward biased. The stored charge in capacitor 582 is fed through resistor 574 to transistors 570 and 576 turning them on. Transistor 578 base drive flows through resistor 581 to return path 524. Capacitor 583 is used for line filtering. There is thus provided circuit operator means associated with photoflash unit 160 in a manner which causes the safety discharge operation upon disconnection of the photo flash unit 160 from the apparatus.

There is also provided normally open circuit means associated with both of the photoflash units 160 and 168 connected in controlling relation to the semiconducting switching means 570 which circuit means is closed when the external photoflash unit 168 is connected to the apparatus to turn transistor 570 on and complete the secondary discharge path. To this end, the transistor base terminal 572 is connected by a line 588 through an interlock 590 to a resistor 592 within the external unit 168 which resistor, in turn, is connected through an interlock 596 and a line 598 to the interlock 210 associated with regulator 104 in FIG. 3. Accordingly, when the external photoflash unit 168 is connected to the apparatus, the foregoing circuit is closed to provide base drive to transistors 572 to complete the secondary discharge path.

The circuit also includes a network of protective diodes 604,608 and 610. In particular, the anode of diode 604 is connected by line 612 to the junction of switch terminal 484 and line 492. The cathode of diode 604 is connected to the anode of diode 608, and the cathode of diode 608 is connected through a fixed resistor 614, a variable resistor 616, an interlock 618, and a line 620 to the circuit associated with comparator 190 shown in FIG. 2. The anode of diode 610 is connected to line 490, and the cathode is connected to the junction of diode 608 and resistor 614. The series combination of diodes 604 and 608 isolates the voltage on capacitor 516 from the electrical connectors of the photoflash unit 160. The combination of diodes 604,608 and 610 provides protection against a current surge in a situation where capacitor 516 of unit 160 is fully charged and the unit 168 is connected to the apparatus with the capacitor thereof uncharged. The arrangement of diodes prevents the flow of heavy current into the capacitor of unit 168.

By way of example, in an illustrative circuit, capacitor 516 has a magnitude of 600 microfarads at 330 volts, resistor 544 has a magnitude of 820 kilohms and capacitor 546 has a magnitude of 0.05 microfarads. Resistor 558 has a magnitude of 1 kilohm and resistor 566 has a magnitude of 220 ohms. Resistor 568 has a magnitude of 100 ohms, resistor 574 a magnitude of 1.5 kilohms, resistor 581 a magnitude of 12 kilohms, capacitor 582 a magnitude of 330 microfarads and resistor 587 a magnitude of 1 kilohm. Resistor 592 has a magnitude of 1 kilohm, resistor 614 has a magnitude of 499 kilohms, and resistor 616 has a magnitude of up to 100 kilohms.

The second photoflash light source and associated circuitry of unit 168 is substantially similar to that of unit 160. It includes a tubular photoflash lamp 630 having terminals 632,634 at opposite ends thereof and a trigger terminal 638. Lamp 630 corresponds to lamp 68 in the illustrative arrangement of FIG. 1 and is removably connected mechanically and electrically to the apparatus by suitable means. There is provided a capacitor 640 similar to capacitor 516 of unit 160, and one terminal of capacitor 640 is connected by a line 642 to the lamp terminal 632, and the opposite terminal of capacitor 640 is connected by a line 644 to the lamp terminal 634. The capacitor terminal connected to line 642 also is connected to line 496 which is connected through the interlock 494 to the photoflash unit 160. The other terminal of capacitor 640 is connected through a line 648, an interlock 650, and a line 652 to line 524 in the circuit of unit 160. The external unit 168 also includes a trigger transformer 660 having a primary winding 662 and a secondary winding 664. One terminal of secondary winding 664 is connected by a line 668 to the lamp trigger terminal 638, and the other winding terminal is connected by a line 670 to line 648. One terminal of primary winding 662 is connected through a current limiting resistor 674 to line 496 and the same winding terminal is connected through a capacitor 678 to line 648. Resistor 674 and capacitor 678 perform the same functions as resistor 544 and capacitor 546 in the circuit of unit 160. The other terminal of primary winding 662 is connected to the anode of a silicon controlled rectifier 680, the cathode of which is connected to line 670. The control or gate terminal 682 of controlled rectifier 680 is connected through a line 684, an interlock 688, and a line 690 to line 560 in the circuit of unit 160.

The external photoflash unit 168 also includes means for defining a secondary discharge path including the series combination of a resistor 700 and semiconductor switching means or transistor 702 connected across the capacitor 640. Transistor 702 normally is nonconducting and the base terminal 704 thereof is connected to the combination of resistor 710 and transistor 703. Transistor 703 is used in a Darlington configuration with transistor 702. Base drive for transistors 703 and 702 is provided in response to disconnection of external flash unit 168 from the apparatus. Capacitor 706 is charged through diodes 718 and 719, and resistor 717 when unit 168 is connected to the apparatus. In removal of unit 168 from the apparatus, transistor 712 turns on, its base drive path being provided by resistor 714. Capacitor 716 is used to filter the voltage at point 701 to keep transistor 712 from noise related conduction. While transistor 712 is on, charge is pulled off of storage capacitor 706. This charge or current passes through resistor 708 to transistor Darlington pair 702 and 703, rendering it conducting to complete the secondary discharge path.

By way of example, in an illustrative circuit, capacitor 640 has a magnitude 500 microfarads at 330 volts, resistor 674 has a magnitude of 820 kilohms, and capacitor 678 has a magnitude of 0.05 microfarads. Resistor 692 has a magnitude of 75 ohms. Resistors 700,708,710 and 714 have the same magnitude as the corresponding resistors in the internal unit 160. Resistors 592 and 717 have magnitude of 1 kilohm. Capacitor 716 has magnitude of 0.1 microfarads at 50 volts while capacitor 706 has magnitude of 330 microfarads at 16 volts.

In operation, the interlocks 488 and 526 serve to disconnect the flyback converter circuit 150 when the internal photoflash unit 160 is removed from the apparatus for reasons of safety. Also, when the unit 160 is removed, the electrical safety discharge circuit discharges capacitor 516 in less than 250 milliseconds. The steering means or switch 154 directs the charging current to the proper flash capacitor. When the external falsh unit 168 is not used, i.e., not connected to the apparatus, the switch 154 directs the charging current to capacitor 516 of unit 160. When the external unit 168 is connected to the apparatus electrical connections are made through the steering and connector components designated 500, 650, 494, 590, and 688, and operator 500 moves switch arm 480 into engagement with contact 484 with the result that the charging current is directed by switch 154 to capacitor 640 of the external unit. When the external unit 168 is not connected to the apparatus the diodes 604 and 608 operate in series to isolate the voltage on capacitor 516 from any exposed connector components as previously described. When the external unit 168 in discharged condition is connected to the apparatus, then the three diodes 604,608 and 610 serve to prevent the flow of heavy current into the uncharged capacitor 640 as previously described.

When it is desired to operate either of the flash tubes 504,630 when a proper command signal is received from the comparator on line 560, the appropriate one of the silicon control rectifiers 550 and 680 is triggered to pull current through the primary winding of the appropriate trigger transformer 530 and 660. A high voltage pulse on the transformer secondary winding triggers the selected flash tube, 504 or 630 to cause a photoflash, assuming that the corresponding capacitor 516,640 has been properly charged. The capacitors 546 and 678 provide low impedance sources for the respective primary windings 532 and 662. The resistors 544 and 674 limit the respective primary currents to a value well below the holding current of the respective silicon control rectifier.

The resistors 614 and 616 are employed to attenuate the 300 volt capacitor charging signal to a level which is compatible with the circuitry of the comparator 170 in a manner which will be described. Each of the respective circuits has the capacitor voltage set for a specified amount of light output. Since the respective capacitors 516,640 and flash tubes 504,630 can have a wide tolerance, the flash capacitor voltage is set to compensate for these variations. The voltage adjusting components are located on the internal flash printed circuit board. This allows the light output to be set beforehand during manufacture of the apparatus without the need for any adjustment subsequently during actual use.

When the apparatus is used as an ophthalmoscope, the external flash unit 168 can be used to take external pictures of the patient's eye and facial area. When the external unit 168 is disconnected from the apparatus the electrical safety discharge circuit including components 700-719 become activated and discharges the energy storage capacitor in less than 250 milliseconds.

To avoid the possibility of firing both internal and external flash tubes 504,630 only one photoflash capacitor 516,640 is charged at a time. For example, suppose that the external flash unit 168 were to be inserted when the internal flash capacitor 516 was fully charged. As the internal capacitor 516 slowly self-discharged, the capacitor voltage sensing comparator 170 would enable the charging circuit of unit 168. This would charge the external capacitor 640, of unit 168. This would charge the external capacitor 640, then when a picture was to be taken both flashes would go off. Even if two separate trigger circuits were used, the energy levels in the vicinity of the fired tube would be high enough to fire the other tube. To avoid this possibility the internal flash capacitor 516 is held in a discharged state, whenever the external flash module 168 is inserted in the apparatus. This is accomplished by providing bias voltage through resistor 592 in the external unit 168 to transistor 570 in the internal flash unit 160. Transistor 570 turns on discharging the internal flash capacitors 516. When the external flash unit 168 is removed, transistor 570 is off and charging of the internal capacitor 516 continues.

FIG. 6 illustrates in further detail circuits for the comparison means 170, the visual indicating means 180, the optical switch 196 and the delay comparator 190 of FIG. 2. The comparison means 170 includes a comparator 720 which is another stage of the single chip integrated circuit previously described. Comparator 720 has an output terminal 722, a non-inverting input terminal 724, and an inverting input terminal 726. Output terminal 722 is connected through a resistor 732 to the non-inverting input terminal 724. The input terminal 724 also is connected through the series combination of resistors 734 and 736 to line 256 in the circuit of FIG. 2. A switch 740 is connected across resistor 736 for removing it from the circuit if desired. The non-inverting input terminal 724 also is connected to line 620 in the circuit of FIG. 5 for sensing the capacitor voltage in a manner which will be described. The inverting input terminal 726 is connected through a resistor 744 to line 250 in the circuit of FIG. 3. Input terminal 726 also is connected through the capacitor 746 to line 256 in the circuit of FIG. 3 and by a line 748 leading to the delay comparator circuit 190 in a manner which will be described. The output terminal 722 of comparator 720 is connected to line 310 in the circuit of FIG. 3 for controlling the operation of transistor 304 in the manner previously described.

The combination of resistors 614 and 616 in the circuit of FIG. 5 and the connection thereof to the capacitors 516 or 640, depending upon the position of switch 154, comprises sensing means for providing a signal proportional to the level of energy stored in the energy storing and releasing means. In particular, the resistors attenuate the voltage to a level compatible with the comparator 720. The resistor 744 and connection to circuit 104 provides a reference voltage on the inverting input terminal 726 for comparison with the capacitor voltage 620 applied to input terminal 724. When the capacitor voltage is below the reference voltage, the output of comparator 720 is low thereby turning on the transistor 304 to allow passage of clock pulses to the flyback converter 150 in the manner previously described. The capacitor voltage continues to be sensed, and when the divided down voltage applied to input terminal 724 exceeds the reference voltage on the input terminal 726 the output on comparator terminal 722 goes high. This causes two events to occur, the first being that hysteresis is added to the noninverting input 724 and the second event being the turning off of transistor 304 to turn off the charging circuit. The capacitor when fully charged will have about 1.2 volts ripple thereon and this ripple voltage is set by the amount of hysteresis in the voltage comparator circuit. Ripple voltage frequency is determined by the discharge rate of the capacitor, the amount of hysteresis in the voltage comparator and the charging rate of the capacitor.

By way of example, in an illustrative circuit, resistor 732 has a magnitude of 1 megohm, resistor 734 a magnitude of 8.45 kilohms, resistor 736 a magnitude of 619 ohms, resistor 744 a magnitude of 1 kilohm and capacitor 746 a magnitude of 0.1 microfarads.

The visual indicating means 180 is shown in further detail in FIG. 6 and includes a first electrically-operated visual indicating means in the form of a light-emitting diode 760 for providing a visual signal in response to a signal from the monitoring means or comparator 170. The light emitting diode 760 can have a characteristic color, for example green. The indicating means 180 also includes a second electrically-operated visual indicating means in the form of a light-emitting diode 762 for providing a visual indication in response to a predetermined condition in the apparatus. For example, in photographic apparatus, such condition could be that the camera is out of film or that the back slide in a fresh pack of film inserted in the camera has not been ejected. Diode 762 can have a characteristic color, for example red. The diodes are connected in reverse poled relation with the anode of diode 760 and cathode of diode 762 connected to terminal 764, and with the cathode of diode 760 and anode of diode 762 connected to terminal 766. The terminal 764 is controlled by the output of comparator 170 in the following manner. The comparator output terminal 722 is connected to the cathode of a diode 768, the anode of which is connected through a resistor 770 to line 258 in the circuit of FIG. 3 having the reference voltage +V. The anode of diode 768 is connected by a line 774 to the base terminal of an NPN transistor 776. The collector of transistor 776 is connected to line 98 in the circuit of FIG. 3 having the voltage $V_{XFMER}$. The emitter of transistor 776 is connected through a resistor 780 to terminal 764.

In order to signal conditions in the apparatus, for example the two illustrative camera situations mentioned above, there is provided a first normally-open switch 784 in the apparatus which closes in response to the condition, for example when the camera is out of film. A second normally-open switch 786 is provided and closes in response to another condition, for example when the film back slide is present. The switches 784,786 are connected together in parallel between the terminals 788,789. Terminal 788 is connected by a line 790 to the junction of resistor 780 and terminal 764 and is connected further through the series combination of diodes 792,794 to the base terminal of transistor 776. The diodes are poled in the same direction with the anode of diode 794 being connected to the base terminal of transistor 776. The other switch network terminal 789 is connected to a complementary voltage follower network generally designated 800. In particular, the voltage follower includes an NPN transistor 802 and a PNP transistor 804 with the respective base and emitter terminals being joined. In particular, the common emitter terminal 806 is connected by line 808 to the diode network terminal 766. The common base terminal 810 is connected through resistors 812 and 814 to the collector terminal of transistor 802. The junction of resistors 812,814 is connected to line 98 in the circuit of FIG. 3 having the voltage $V_{XFMER}$. The common base terminal 810 is connected through a resistor 816 to the collector terminal of transistor 804, and the junction of resistor 816 and the collector of transistor 804 is connected by a line 820 to the switch network terminal 789. Line 820 also is connected to line 374 in the circuit of FIG. 3.

The indicator means 180 including the dual color light emitting diodes 760 and 762 indicates the following conditions. The indicator is green when the capacitor 516 or 640 of either flash unit is fully charged and the camera is ready for picture taking. A red indicator signals that the camera is out of film or that the back slide in the fresh pack of film has not been ejected. When the instrument has power applied thereto and the indicator is not on this indicates that the flash capacitor is still charging.

During the mode of operation when the capacitor is still being charged, the output of comparator 720 is low which causes diode 768 to conduct with the result that a relatively low signal is on line 774 rendering transistor 776 nonconducting. When the flash capacitor is fully charged the output of comparator 720 is high blocking the diode 768 with the result that a relatively higher voltage is on line 774 thereby turning transistor 776 on. This, in turn, applies a relatively high voltage to terminal 764 and also to the anode of diode 760 causing it to conduct. At the same time under these conditions diode 762 is non-conducting. Thus, there is a flow of current from the supply line 98 through transistor 776, resistor 780 and the green diode 760 to the emitters of transistors 802 and 804. The transistors 802, 804 act as a complementary voltage follower of the voltage established by resistors 812 and 816. Normally this buffered voltage is about one-third that of the voltage Vx on line 98. When the camera is out of film or the back slide is present either of the switches 784,786 is closed. The switch closure then places the cathode of diode 762 at the ground or reference voltage level by means of the connection of terminal 764 through line 790 and the closed switch to line 374. Current then flows out of the complementary voltage follower to the diode 762. If during the foregoing situation transistor 776 were on, in this illustrative circuit a current of around 300 milliamperes would flow through resistor 780 and transistor 776 were it not for the current limiting action provided by diodes 792 and 794, resistor 780 and transistor 776. The active current limiting reduces the current to levels less than 20 millamperes. Accordingly, this portion of the circuit together with the complementary voltage follower 800 acts as a priority circuit operatively connected to both of the visual indicating means or diodes 760, 762 to give priority to operation of the diode 762. In addition, the complementary voltage follower 800 may be viewed as operating as a current source for the first indicating means or diode 760 and as a current sink for a second indicating means or diode 762.

By way of example, in an illustrative circuit, resistor 780 has a magnitude of 39 ohms, resistor 812 a magnitude of 2 kilohms, resistor 814 a magnitude of 270 ohms and resistor 816 a magnitude of 1 kilohm.

The delay comparator 190 and optical switch 196 comprise delay circuit means operatively connected to the photoflash light source and to means for commanding operation of the photoflash light source for providing a predetermined time delay between the occurrence of a command and the actual operation of the photoflash light source. The delay circuit includes an RC timing circuit comprising the series combination of a resistor 840 and capacitor 842 with one terminal of resistor 840 being connected to line 258 in the circuit of FIG. 3 and having the voltage $+V$. There is also provided semiconductor switching means in the form of a phototransistor 846 connected in controlling relation to the capacitor of the RC circuit, the switching means having a first state maintaining the capacitor in a discharged state and a second state allowing the capacitor to charge. In particular, the collector terminal of transistor 846 is connected by a line 848 to the junction of capacitor 842 and resistor 840, and the emitter of transistor 846 is connected by a line 850 to the other terminal of capacitor 842. This capacitor terminal also is connected to line 748 from the comparator circuit 170. There is also provided control means operatively associated with the transistor 846 for placing the transistor in the second state in response to means for commanding operation of the photoflash light source. In particular, a light emitting diode 854 normally directs light to the base of transistor 846, and the light beam is interrupted by an operator member generally designated 856, mechanically associated with the photographic apparatus, in response to a command for operation of the photoflash lamp. For example, member 856 can be a vane moved into position interrupting the light beam from diode 854 to transistor 846 when the person operating the apparatus pushes a button to operate the photoflash and take a picture. The anode of diode 854 is connected through a resistor 858 to line 98 having the voltage $V_{XFMER}$, and the cathode of diode 854 is connected by a line 860 to the emitter of transistor 846.

The delay circuit means also includes a comparator 870 which is another stage of the single chip integrated circuit comparator previously described. Comparator 870 has an output terminal 872, an inverting input terminal 874, and a noninverting input terminal 876. The inverting input terminal 874 is connected to line 250 in the circuit of FIG. 3. The non-inverting input terminal 876 is connected through a resistor 880 to the junction of capacitor 842 and resistor 840. Output terminal 872 is connected to input terminal 876 through a resistor 882, and output terminal 872 is connected through a resistor 884 to line 258 in the circuit of FIG. 3 having the voltage $+V$. The output terminal 872 of comparator 870 also is connected to line 564 in the photoflash circuits of FIG. 5.

The optical switch delay circuit is used to delay the firing of the photoflash light source until the mirrors and other optics in the apparatus have settled. A number of events occur in a sequence to fire the flash. First the equipment operator pushes a button or other manually-operated element causing the operator member of flag 856 to obscure the light beam from diode 854 to transistor 846. As a result, phototransistor 846 is turned off and delay capacitor 842 is allowed to charge through resistor 840. When the voltage on capacitor 848 is slightly more than the reference voltage on comparator terminal 874, the output terminal of compartor 870 goes positive. Hysteresis is used to keep the comparator from oscillating. The positive comparator output then is applied through line 564 to the appropriate circuit to fire the associated photoflash lamp. Typically, the time delay from breaking of the optical switch light beam to the firing of the photoflash is about 25 milliseconds.

By way of example, in an illustrative circuit, resistor 840 has a magnitude of about 430 kilohms and capacitor 842 has a magnitude of 0.001 microfarad. Resistors 880 and 884 have magnitudes of 1 kilohm and resistor 882 is a one megohm resistor. Resistor 858 has a magnitude of 560 ohms.

The circuit of the present invention operates in the following manner. Assume that only the internal photoflash light source and associated circuit 160 is mechanically and electrically connected to the apparatus. The switch arm 480 of the high voltage steering means 154 shown in FIG. 5 thus engages contact 482. The clock pulse generator 110 including comparator stage 260 applies clock pulses to the pulse width modulator circuit 128 including comparator stage 396 to operate the viewing lamp 134. The intensity of light provided by lamp 134 is adjusted according to the setting of the potentiometer 452 in the circuit of FIG. 4, and any changes in the voltage Vx from the power supply are compensated for by the negative feedback provided through the resistors 450 and 452 to the comparator input terminal 402. At the same time, the clock pulse generator 110 applies pulses through the transistor switch 304 in FIG. 3 to the flyback converter circuit 150. As previously described, the pulse waveform in the primary circuit of flyback transformer 326 causes a stepped up voltage in the secondary circuit which is applied by line 370 through switch arm 480 and contact 482 in FIG. 5 to the capacitor 516 for charging the same. The voltage increase on capacitor 516 during charging thereof is sensed through the network of attenuating resistors 614, 616 and applied by line 620 to the comparator 170, in particular to the input terminal 724 of comparator stage 720 shown in FIG. 6. When the capacitor voltage reaches a predetermined desired value, as set by the reference value applied to input terminal 726 of the comparator stage 720, the transistor 304 is turned off as previously described to stop further application of clock pulses to the flyback converter 150 and thereby stop the charging of capacitor 516. Accordingly, the charge on capacitor 516 is at the desired level for operating the lamp 504 upon demand.

In the illustrative use of the circuit in an ophthalmoscope. during the foregoing mode of operation the practitioner utilizes the light from the viewing lamp 134 to examine the eye of the patient and to make the necessary adjustments and alignments for making a photographic record thereof. Assuming that the capacitor voltage has reached the desired value and that neither of the switches 784, 786 in the circuit of FIG. 6 is closed, the green colored light emitting diode 760 is operated thereby signalling to the practitioner that the apparatus is ready for picture taking. When that is desired, the practitioner operates the appropriate control, such as a manually-operated push button as previously described, causing the member 856 in FIG. 6 to interrupt the beam of light from diode 854 to transistor 846 thereby turning off the transistor and allowing capacitor 842 to charge. When the voltage on capacitor 842 reaches the required value, after the predetermined time delay, the comparator stage 870 provides an output in the form of a command signal on line 564 applied to the gate of silicon controlled rectifier 550 in FIG. 5 thereby firing the rectifier to operate trigger transformer 530 to fire the photoflash lamp 504. During firing of lamp 504 the capacitor 516 is discharged therethrough.

After operation of lamp 504, the reduced or zero voltage on capacitor 516 is sensed with the result that transistor 304 is again turned on and the flyback converter 150 is operated to cause re-charging of capacitor 516. The viewing lamp 134 continues to operate.

Assume now that it is desired to connect the external photoflash light source and associated circuit 168 to the apparatus for making a photographic record of the external portion of the patient's eye or neighboring facial area. The mechanical and electrical connection of the external source 168 to the apparatus causes operator element 500 to move switch arm 480 into engagement with contact 484 in FIG. 5. As previously described, and tendency of heavy currents to flow to the uncharges capacitor 640 of the external unit 168 is prevented by the protective network of diodes 604, 608 and 610. Also, upon connection of unit 168 to the apparatus, the circuit including line 598, resistor 592 and line 588 in FIG. 5 is completed to apply a relatively high voltage to the base of transistor 570 turning it on and providing a discharge path for capacitor 516 of the internal flash unit 160 through resistor 568 and transistor 572 to the reference line 524.

During the foregoing, the viewing lamp 134 is operated thereby allowing use by the practitioner as previously described. The capacitor 640 is charged in a manner identical to that of capacitor 516, including sensing of the voltage thereon by the comparator 170, and when it is desired to operate the lamp 630 this is done on a manner similar to that of the internal unit 160 with the same time delay provided by resistor 840 and capacitor 842 in the circuit of FIG. 6. A command signal then appears on line 564 and is applied through line 690 to the gate of silicon control rectifier 680. The operation of the trigger transformer causes firing of lamp 630 to operate the same with capacitor 640 discharging therethrough. After firing of the lamp 630, the capacitor 640 is recharged.

Subsequently, if the external unit 168 is removed from the apparatus the electrical safety discharge circuit including components 700–719 becomes activated, and base drive is applied to transistor 702 causing it to turn on. This completes the secondary discharge path for capacitor 640 through resistor 700 and transistor 702. Similarly, in the event that the internal unit 160 is removed from the apparatus, this activates the internal electrical safety discharge circuit including components 570–587 discharging energy storage capacitor 516 in less than 250 milliseconds. The foregoing occurs before either of the units is completely mechanically disengaged from the apparatus whereby each secondary discharge path is to the main circuit reference or ground.

It is therefore apparent that the present invention accomplishes its intended objects. The foregoing safety measures as described including the operation of high voltage steering means 154, the protective diode network 602, 608 and 610, the circuit including resistor 592, and the safety discharge circuits prevent electrical hazards when the photoflash light sources 160 and 168 and connected to and disconnected from the apparatus. The combination of the optical switch 196 and delay circuit 190 allows the optics in the apparatus to reach a steady condition before operation of the photoflash light source. The arrangement of the source of clock pulses 110, flyback converter 150, high voltage steering means 154, comparator 170, and indicating means 180 enables accurate and effective control of voltage for operating the photoflash light sources. The comparator stages of the clock pulse generator, pulse width modulator, comparator, and delay circuit all are provided by a single chip integrated circuit thereby utilizing the advantages provided thereby.

While a single embodiment of the present invention has been described in detail, this is for the purpose of illustration, not limitation.

I claim:

1. In optical apparatus for viewing an object and making a photographic record thereof and having a photoflash light source;
   (a) an electrically operated illuminating light source for illuminating the object during viewing prior to operation of said photoflash light source, said illuminating light source having an intensity proportional to the width of electrical pulses applied thereto;
   (b) pulse generating means operatively connected to said illuminating light source for applying electrical pulses of controlled width to said light source for operating the same;
   (c) energy storing and releasing means connected to said photoflash light source for storing energy and releasing said stored energy to said photoflash light source upon demand for photoflash operation thereof;
   (d) conversion circuit means operatively connected to said energy storing and releasing means for converting electrical pulses applied thereto into energy to be stored for use in operating said photoflash light source; and
   (e) a source of clock pulses operatively connected to said pulse generating means for operating the same and operatively connected to said conversion circuit means for supplying the pulses to be converted thereby.

2. Apparatus according to claim 1, further including means for directing light along a given path into an eye for illumination of its fundus and means for viewing the illuminated fundus to align and focus said apparatus thereupon thereby providing an ophthalmic photographic recording instrument.

3. Apparatus according to claim 1, further including energy level control means operatively connected to said energy storing and releasing means and to said conversion circuit means for stopping the application of pulses from said clock pulse source to said conversion circuit means when the level of stored energy reaches a predetermined amount.

4. Apparatus according to claim 3, wherein said energy level control means comprises:

(a) sensing means operatively connected to said energy storing and releasing means for providing a signal proportional to the level of stored energy;
(b) comparison means having an output, a first input connected to said sensing means and a second input connected to means providing a reference signal, said comparison means providing an output signal when said signal from said sensing means equals said reference signal; and
(c) normally-closed controlled switching means connected between said source of clock pulses and said conversion circuit means and having a control input connected to the output of said comparison means, said switching means opening in response to said output signal from said comparison means to disconnect said source of clock pulses from said conversion circuit means when said energy level reaches said predetermined amount.

5. Apparatus according to claim 4, further including electrically-operated visual indicating means connected to the output of said comparison means for providing a visual signal in response to said output signal from said comparison means.

6. Apparatus according to claim 5, further including:
(a) another electrically-operated visual indicating means;
(b) first circuit means operatively connected to said other visual indicating means and to said apparatus for operating said visual indicating means in response to a predetermined condition in said apparatus; and
(c) second circuit means operatively connected to both of said visual indicating means to give priority to operation of said other visual indicating means.

7. Apparatus according to claim 1, further including delay circuit means operatively connected to said photoflash light source and to means for commanding operation of said photoflash light source for providing a predetermined time delay between the occurrence of a command and the actual operation of said photoflash light source.

8. Apparatus according to claim 7, wherein said delay circuit means comprises:
(a) an R-C timing circuit;
(b) semiconductor switching means connected in controlling relation to the capacitor of said R-C circuit, said switching means having a first state maintaining said capacitor in a discharged state and a second state allowing said capacitor to charge;
(c) control means operatively associated with said semiconductor switching means for placing said switcing means in said second state in response to said means for commanding operation of said photoflash light source;
(d) comparison means having a first input connected to means providing a reference voltage, a second input connected to said capacitor, and an output; and
(e) means for coupling said output of said comparison means to said photoflash light source for causing operation of said source in response to an output from said comparison means;
(f) whereby when said semiconductor switching means is changed to said second state said capacitor becomes charged and after a delay determined by said R-C timing circuit the voltage on said capacitor reaches a level causing said comparison means to provide an output signal causing operation of said photoflash light source.

9. Apparatus according to claim 8, wherein said semiconductor switching means comprises a phototransistor, and wherein said control means comprises a light-emitting diode adapted to illuminate and operate said phototransistor and means connected to said command means to control the light beam from said diode to said transistor.

10. Apparatus according to claim 1, further including:
(a) an additional photoflash light source;
(b) an additional energy storing and releasing means connected to said additional photoflash light source for storing energy and releasing said energy on demand to said light source for photoflash operation thereof; and
(c) switching means for connecting the output of said conversion circuit means to either of said energy storing and releasing means for causing energy to be stored in only one of said energy storing and releasing means at a time.

11. Apparatus according to claim 10, wherein said additional photoflash light source is removably connected to said apparatus, and further including operator means associated with said switching means for causing said switching means to connect said conversion circuit means to said additional energy storing and releasing means when said additional photoflash light source is connected to said apparatus.

12. Apparatus according to claim 10, wheren at least one of said photoflash light sources and associated energy storing and releasing means is removably connected to said apparatus and further including protection means for preventing a current surge from a charged energy storing and releasing means to an uncharged energy storing and releasing means when said removable energy storing and releasing means is connected to said apparatus.

13. Apparatus according to claim 12, wherein said protection means comprises diode circuit means adapted to be connected to said removable energy storing and releasing means for providing a discharge path for stored energy therein.

14. Apparatus according to claim 10, wherein said additional photoflash light source and associated energy storing and releasing means is removably connected to said apparatus, and further including means in said additional energy storing and releasing means for discharging energy stored therein when said additional photoflash light source and associated energy storing and releasing means is removed from said apparatus.

15. Apparatus according to claim 10, wherein said additional photoflash light source and associated additional energy storing and releasing means is removably connected to said apparatus, and further including means for defining an additional discharge path for removing stored energy from said first-named energy storing and releasing means when said additional photoflash light source and energy storing and releasing means is connected to said apparatus.

16. In optical apparatus for viewing a subject and making a photographic record thereof having an illuminating light source for illuminating the subject during viewing and providing light having an intensity proportional to the width of electrical pulses applied thereto and said apparatus having a photoflash light source operated by a capacitor discharge circuit to which energy is supplied by a flyback transformer circuit, the improvement comprising means for controlling the operation of said illuminating light source and said photoflash light source in the form of a single chip integrated circuit having a plurality of comparator stages, each of said stages having an output, an inverting input and a non-inverting input, wherein:
(a) a first stage of said comparator has the inputs thereof connected to an R-C network to provide system clock pulses at the output thereof;
(b) a second stage of said comparator has the output thereof coupled to said illuminating light source, the inverting input thereof connected to a ramp generating circuit coupled to the output of said first comparator stage, and the non-inverting input thereof connected to a negative feedback circuit connected to said light source, whereby said second comparator stage is connected as a pulse width modulator for supplying pulses of adjustable width to said illuminating light source;
(c) a third stage of said comparator has the non-inverting input thereof connected to means for sensing the voltage on the capacitor of the discharge circuit associated with said photoflash light source, has the inverting input thereof connected to means providing a reference voltage, and has the output thereof connected in controlling relation to switch means coupling the output of said first comparator stage to said flyback transformer circuit, whereby when the sensed voltage on said capacitor reaches the level of the reference voltage said comparator operates said switch to stop application of clock pulses to said transformer circuit to stop further charging of said capacitor; and
(d) a fourth stage of said comparator has the output thereof connected to said capacitor discharge circuit in a manner such that discharge of the capacitor occurs in response to an output from said comparator, has the inverting input thereof connected to means providing a reference voltage, and has the non-inverting output thereof connected to the capacitor of an R-C timing circuit including means for initiating charging of said capacitor in response to a command to operate said photoflash whereby after a time delay determined by said R-C circuit said comparator provides an output to cause operation of said photoflash light source.

17. Apparatus according to claim 16, further including means for directing light along a given path into an eye for illumination of its fundus and means for viewing the illuminated fundus to align and focus said apparatus thereupon thereby providing an ophthalmic photographic recording instrument.

18. In an ophthalmic photographic recording instrument including means for directing light along a given path into an eye for illumination of its fundus and means for viewing the illuminated fundus to align and focus said instrument thereon, the improvement comprising:
(a) a flash unit including a photoflash light source and a circuit for operating said source including a capacitor and voltage determining components for said capacitor;
(b) charging circuit means for providing voltage for charging said capacitor;
(c) voltage sensing and comparing means connected in controlling relation to said charging circuit means for stopping the operation of said charging circuit means when the sensed voltage reaches a predetermined value; and (d) means for removably connecting said circuit of said flash unit to said charging circuit means and to said voltage sensing and comparing means for charging said capacitor in a manner controlling the voltage on said capacitor whereby the light output from said photoflash light source can be pre-set without any need for adjustment after said flash unit is connected to said instrument.

19. In optical apparatus for viewing an object and making a photographic record thereof:
  (a) a first photoflash light source and associated energy storing and releasing means for storing energy and releasing said stored energy to said photoflash light source upon demand for photoflash operation thereof;
  (b) a second photoflash light source and associated energy storing and releasing means for storing energy and releasing said stored energy to said photoflash light source upon demand for photoflash operation thereof, said second photoflash light source and associated energy storing and releasing means being removably connected to said apparatus;
  (c) means for providing energy to operate said photoflash light sources;
  (d) switching means operatively connected to said energy providing means having a first state connecting said energy providing means to said first energy storing and releasing means and having a second state connecting said energy providing means to said second energy storing and releasing means, said switching means normally being in said first state;
  (e) operator means associated with said second photoflash light source and associated energy storing and releasing means for changing said switching means to said second state when said second photoflash light source and associated energy storing and releasing means is connected to said apparatus; and
  (f) means operatively associated with said first and second photoflash light sources and associated energy storing and releasing means for defining another discharge path from said first energy storing and releasing means when said second photoflash light source and associated energy storing and releasing means is connected to said apparatus.

20. Apparatus according to claim 19, wherein said first energy storing and releasing means includes a capacitor and wherein said discharge path defining means comprises:
  (a) normally open semiconductor switching means connected across said capacitor in a manner to define a discharge path for said capacitor when said switching means becomes closed; and
  (b) normally open circuit means in said first and second photoflash light sources and associated energy storing and releasing means and connected in controlling relation to said switching means, said circuit means being closed in response to connection of said second photoflash light source and associated energy storing and releasing means to said apparatus to cause closing of said semiconductor switching means to complete said discharge path for said capacitor.

21. Apparatus according to claim 19, further including means for directing light along a given path into an eye for illumination of its fundus and means for viewing the illuminated fundus to align and focus said apparatus thereupon providing an ophthalmic photographic recording instrument, said first photoflash light source being located in said apparatus for directing a photoflash to the fundus during photographing of the same, and said second photoflash light source being located for directing a photoflash to a different part of the object being photographed.

22. In an ophthalmic photographic recording instrument including means for directing light along a given path into an eye for illumination of its fundus and means for viewing the illuminated fundus to align and focus said instrument thereon:
  (a) first and second flash units removably connected to said apparatus, each of said flash units including a photoflash light source and a circuit including a capacitor for operating said light source upon discharge through a primary discharge path;
  (b) charging circuit means for charging either of said capacitors of said flash units; and
  (c) each of said flash unit circuits including means for defining a secondary discharge path for the capacitor thereof in response to disconnection of that flash unit from said apparatus.

23. Apparatus according to claim 22, wherein each of said secondary discharge path defining means comprises:
  (a) normally open semiconductor switching means connected across said capacitor in a manner to define said secondary discharge path for said capacitor when said switching means becomes closed; and
  (b) normally open circuit means connected in controlling relation to said switching means, said circuit means being closed in response to disconnection of the particular flash unit from said apparatus to cause closing of said semiconductor switching means to complete said secondary discharge path.

24. In an ophthalmic photographic recording instrument including means for directing light along a given path into an eye for illumination of its fundus and means for viewing the illuminated fundus to align and focus said instrument thereon:
  (a) an electrically operated illuminating light source for illuminating the fundus and having a light intensity proportional to the width of electrical pulses applied thereto;
  (b) a comparator circuit having an output, an inverting input and a non-inverting input;
  (c) means for coupling said output of said comparator to said light source;
  (d) circuit means including a source of clock pulses, a differentiator and ramp generator for providing a sawtooth waveform and connected to said inverting input of said comparator; and
  (e) a negative feedback circuit connected between said light source and said non-inverting input of said comparator; whereby
  (f) said comparator circuit operates as a pulse width modulator to supply pulses of adjustable width to said illuminating light source.

25. Apparatus according to claim 24, wherein said negative feedback circuit includes adjustable resistance means for controlling the intensity of said illuminating light source.

26. In optical apparatus for viewing an object and making a photographic record thereof;
  (a) a photoflash light source and energy storing and releasing means for storing energy and releasing said stored energy to said photoflash light source upon demand for photoflash operation thereof;

(b) means for providing energy to operate said photoflash light source;

(c) energy level monitoring means operatively connected to said energy storing and releasing means for providing a signal when the level of stored energy reaches a predetermined amount;

(d) first electrically operated visual indicating means connected to said monitoring means for providing a visual signal in response to a signal from said monitoring means;

(e) second electrically operated visual indicating means;

(f) circuit means operatively connected to said second visual indicating means and to said apparatus for operating said second visual indicating means in response to a predetermined condition in said apparatus; and (g) priority circuit means operatively connected to both of said visual indicating means to give priority to operation of said second visual indicating means.

27. Apparatus according to claim 26, wherein said priority circuit means comprises:

(a) a complementary voltage follower operatively connected to said circuit means of said second visual indicating means, said follower connected to operate as a current source for said first indicating means and a current sink for said second indicating means; and (b) current limiting circuit means operatively connected to said monitoring means and to said first indicating means.

* * * * *